United States Patent [19]

Fauchere et al.

[11] Patent Number: 5,708,016
[45] Date of Patent: Jan. 13, 1998

[54] PSEUDOPEPTIDES DERIVED FROM NEUROKININS

[75] Inventors: Jean-Luc Fauchere, Saint-Cloud; Nathalie Kucharczyk-Gentric, Issy Les Moulineaux; Emmanuel Canet, Paris; Michel Lonchampt, Chevilly La Rue, all of France

[73] Assignee: Adir et Compagnie, Courbevoie, France

[21] Appl. No.: 801,037

[22] Filed: Feb. 14, 1997

[30] Foreign Application Priority Data

Feb. 16, 1996 [FR] France .................... 96 01919

[51] Int. Cl.⁶ .................... A01N 43/713; A61K 31/41
[52] U.S. Cl. .................... 514/381; 548/252
[58] Field of Search ............. 514/381; 548/252

[56] References Cited

FOREIGN PATENT DOCUMENTS 0 684 257 A1  11/1995  European Pat. Off. .

*Primary Examiner*—Paula K. Hutzell
*Assistant Examiner*—Benet Prickril
*Attorney, Agent, or Firm*—The Firm of Gordon W. Hueschen

[57] ABSTRACT

A compound of formula (I):

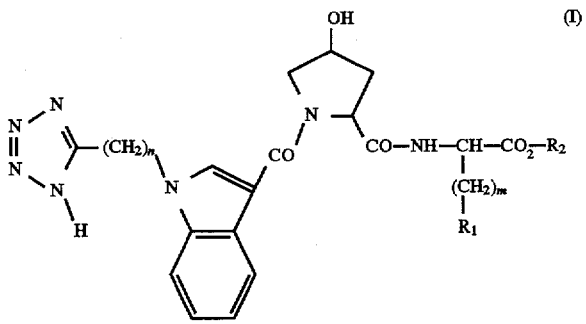

in which:

$R_1$ represents an indolyl, naphthyl, tetrahydronaphthyl, thienyl, phenyl, optionally substituted, or $(C_3-C_7)$ cycloalkyl group, n represents an integer such that $1 \leq n \leq 8$, m represents an integer such that $1 \leq m \leq 4$, $R_2$ represents an unsubstituted or substituted benzyl group, an unsubstituted or substituted phenyl group or a linear or branched $(C_1-C_6)$alkyl group, its enantiomers, diastereoisomers and epimers as well as its addition salts with a pharmaceutically acceptable acid or base, and medicinal products containing the same are useful as substance P antagonists.

9 Claims, No Drawings

PSEUDOPEPTIDES DERIVED FROM NEUROKININS

BACKGROUND OF THE INVENTION

The present invention relates to new pseudopeptides derived from neurokinins.

1. Field of the Invention

The neuorokinins form a family of neuropeptides possessing a structural analogy, namely Phe-X-Gly-Leu-Met-$NH_2$ in the C-terminal portion. These neuropeptides, substance P (SP), neurokinin A (NKA) and neurokinin B (NKB), induce a rapid contraction of smooth muscle fibers, as opposed to the slow contractions developed by bradykinin. They are widely represented in the human body, especially in the central nervous system and the peripheral nervous system, their endogenous agonist effects being accomplished via specific receptors, with a preferential affinity of SP, NKA and NKB for the $NK_1$, $NK_2$ and $NK_3$ receptors. They are involved in numerous physiological or physiopathological processes, such as nociception, vascular permeability, smooth muscle fiber contraction, hypersecretion and immunomodulation (Otsuka M. et al., Physiol. Rev. 73,229–308, 1993).

2. Prior Art Description

Numerous neurokinin-antagordst peptides have been described in the literature. This applies, for example, to the compounds described in Patents EP 333,174, EP 394,989, WO 92/22569 or EP 684,257.

DETAILED DESCRIPTION OF THE INVENTION

The subject of the present invention is synthetic pseudopeptides which, apart from being new, have been shown to be especially useful on account of the intensity of their pharmacological properties. They possess selective and potent antagonist properties in relation to neurokinin receptors, and more especially the $NK_1$ receptors.

These properties mean that they can be used, in particular, in the treatment of pain, inflammatory processes of various origins, gastrointestinal disorders, asthma, chronic bronchopathies, allergies, urological disorders, migraine and diseases of the central nervous system, and also as antiemetics.

The invention relates more especially to the compounds of formula (I):

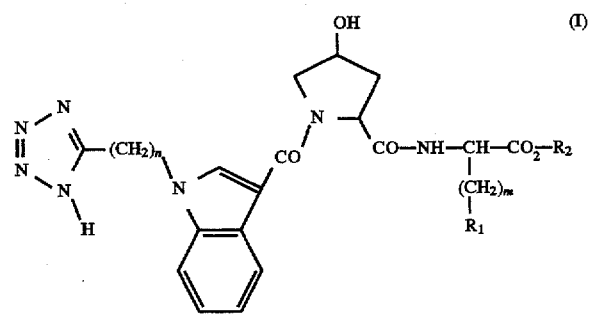

in which $R_1$ represents an indolyl, naphthyl, tetrahydronaphthyl, thienyl, phenyl (optionally substituted with one or more halogen atoms or linear or branched ($C_1$–$C_6$)alkyl, linear or branched ($C_1$–$C_6$)alkoxy, hydroxyl or trihalomethyl groups) or ($C_3$–$C_7$)cycloalkyl group, n represents an integer such that $1 \leq n \leq 8$, m represents an integer such that $1 \leq m \leq 4$, $R_2$ represents a benzyl group (unsubstituted or substituted with one or more halogen atoms or linear or branched ($C_1$–$C_6$)alkyl, linear or branched ($C_1$–$C_6$)alkoxy, hydroxyl or trihalomethyl groups), a phenyl group (unsubstituted or substituted with one or more halogen atoms or linear or branched ($C_1$–$C_6$)alkyl, linear or branched ($C_1$–$C_6$)alkoxy, hydroxyl or trihalomethyl groups) or a linear or branched ($C_1$–$C_6$)alkyl group, their enantiomers, diastereoisomers and epimers as well as their addition salts with a pharmaceutically acceptable acid or base.

Among pharmaceutically acceptable acids, there may be mentioned, without implied limitation, hydrochloric, hydrobromic, sulfuric, phosphonic, acetic, trifluoroacetic, lactic, pyruvic, malonic, succinic, glutaric, fumaric, tartaric, maleic, citric, ascorbic, oxalic, methanesulfonic and camphoric, and the like, acids.

Among pharmaceutically acceptable bases, there may be mentioned, without implied limitation, sodium hydroxide, potassium hydroxide, triethylamine, tert-butylamine, and the like.

Preferred compounds of the invention are those for which $R_1$ represents an indolyl group.

The invention also extends to the process for preparing the compounds of formula (I). In one of these processes, a protected hydroxyproline of formula LID, the isomers of which have optionally been separated,

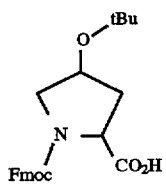

in which:

Fmoc represents a 9-fluorenylmethoxycarbonyl group, tBu represents a tert-butyl group, is reacted with benzyl alcohol in the presence of 4-dimethylaminopyridine and N,N-dicyclohexylcarbodiimide, to yield the compound of formula (III):

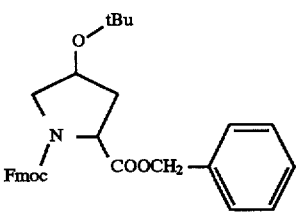

in which Fmoc and tBu have the same meanings as above, the amine function of which is deprotected in a piperidine medium, to yield the compound of formula (IV):

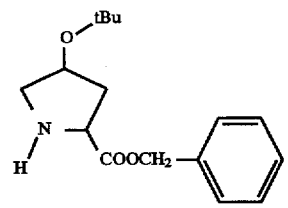

in which tBu has the same meaning as above, which is reacted with 3-indolecarboxylic acid, to yield the compound of formula (V)

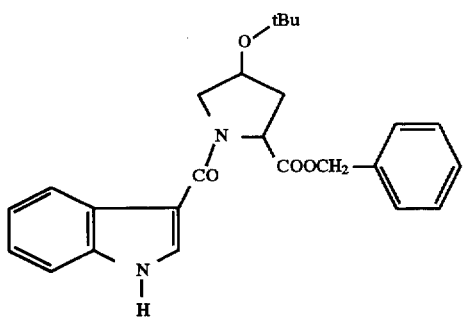

in which tBu has the same meaning as above, the carboxylic acid function of which is deprotected by catalytic hydrogenation, to yield the compound of formula (VI):

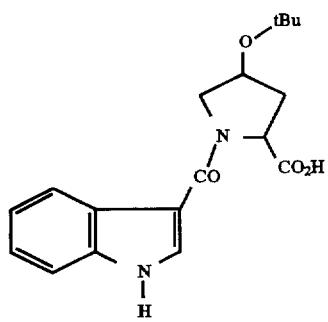

in which tBu has the same meaning as above, which is reacted with a protected amino acid of formula (VII), the isomers of which have optionally been separated:

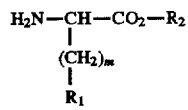 (VII)

in which $R_1$, $R_2$ and m have the same meaning as in the formula (I), to yield the compound of formula (VIII):

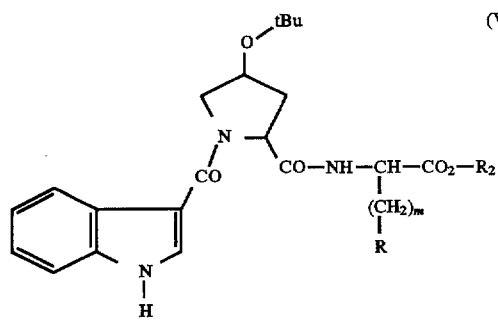

in which tBu, $R_1$, $R_2$ and m have the same meaning as above, which is reacted with a protected tetrazole of formula (IX) in the presence of tetrabutylammonium hydrogen sulfate,

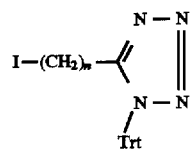 (IX)

in which Trt represents a triphenylmethyl group, to yield the compound of formula (X):

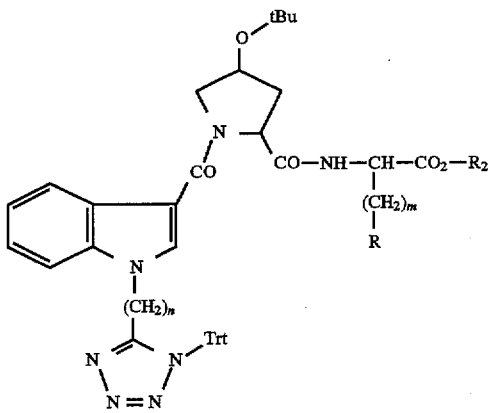

in which tBu, $R_1$, $R_2$, m, n and Trt have the same meaning as above, which is deprotected in a trifluoroacetic acid medium, to yield the compound of formula (I), which can, where appropriate, be purified according to a standard purification technique, the isomers of which are, where appropriate, separated according to a standard separation technique, which is converted, if so desired, to its addition salts with a pharmaceutically acceptable base.

The compound of formula (IX) is obtained by reacting a nitrile of formula (XI):

 (XI)

in which n has the same meaning as in the formula (I), with sodium azide in the presence of aluminium chloride under an inert atmosphere, to yield the compound of formula (XII):

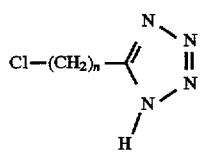 (XII)

in which n has the same meaning as in the formula (I), which is reacted with triphenylmethyl chloride in the presence of triethylamine, to yield the compound of formula (XIII):

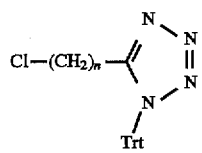 (XIII)

in which n and Trt have the same meaning as above, which is then treated with sodium iodide to yield the corresponding iodinated compound of formula (IX).

In another process for preparing the compounds of formula (I), 3-indolecarboxylic acid benzyl ester is reacted with a bromonitrile of formula (XIV) in the presence of sodium hydride:

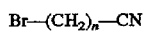 (XIV)

in which n has the same meaning as in the formula (I), to yield the compound of formula (XV)

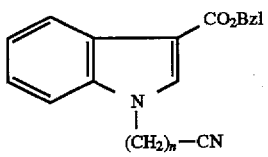

in which n has the same meaning as in the formula (I) and Bzl represents a benzyl group, the acid function of which is deprotected by catalytic hydrogenation, to yield the compound of formula (XVI)

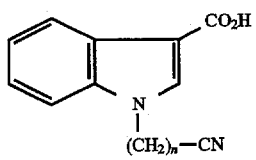

in which n has the same meaning as in the formula (I), which is reacted with a protected hydroxyproline of formula (XVII) in the presence of bromotris(pyrrolidino) phosphonium hexafluorophosphate and diisopropylethylamine:

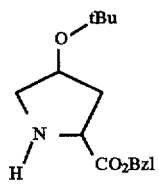

in which tBu represents a tert-butyl group and Bzl a benzyl group, to yield the compound of formula (XVIII):

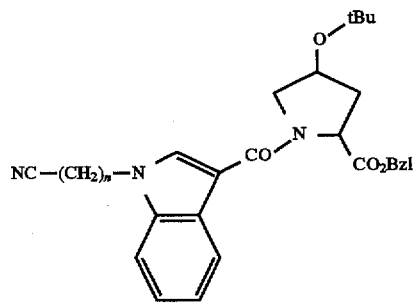

in which n, tBu and Bzl have the same meaning as above, the acid function of which is deprotected in a basic medium in the presence of a catalyst, to yield the compound of formula (XIX):

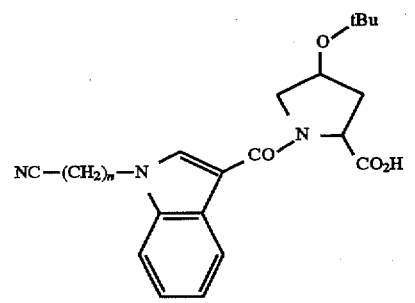

in which n and tBu have the same meaning as above, which is reacted with a compound of formula (XX) in the presence of a peptide coupling reagent:

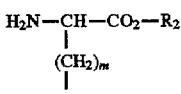

in which $R_1$, $R_2$ and m have the same meaning as in the formula (I), to yield the compound of formula (XXI):

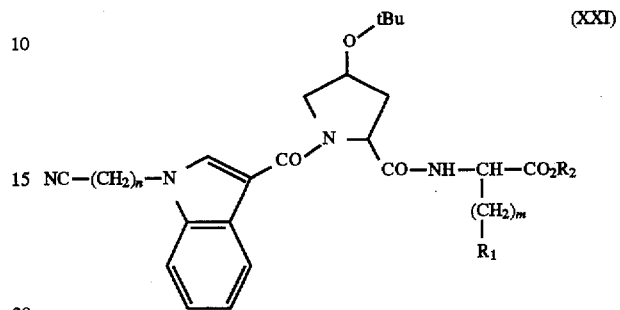

in which $R_1$, $R_2$, n, m and tBu have the same meaning as above, which is then treated with trimethylazidosilane and dibutyltin oxide, to yield the compound of formula (XXII):

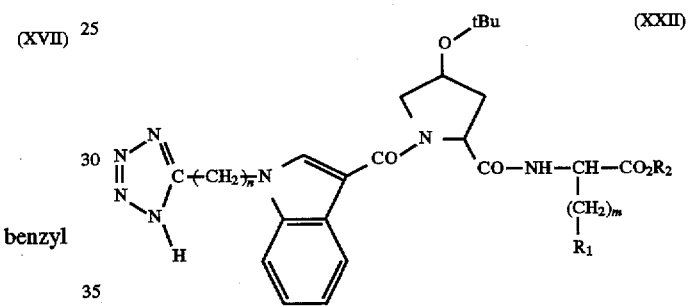

in which $R_1$, $R_2$, n, m and tBu have the same meaning as above, which is deprotected in a trifluoroacetic acid medium to yield the compound of formula (I), which can, where appropriate, be purified according to a standard purification technique, the isomers of which are, where appropriate, separated according to a standard separation technique, which is converted, if so desired, to its addition salts with a pharmaceutically acceptable base.

The compounds of the invention possess very useful pharmacological properties. They are specific ligands for neurokinin receptors, which possess, in particular, especially intense antagonist properties in relation to the $NK_1$ receptors. The $NK_1$ receptors are considered to be involved, more especially, in the regulation of pain transmission, of the edema induced by an increase in vascular permeability, of secretory phenomena at tracheobronchial and gastrointestinal level, of salivation, of ventilatory control and the control of vascular tonus and of the activation of cells that participate in inflammatory processes. Furthermore, contrary to some substance P-antagonist pseudopeptide compounds, these compounds have no degranulating effect on mast cells.

Moreover, apart from being new, the compounds of the present invention have proved especially potent, especially in relation to the closest compounds of the prior art described in Patent EP 684,257. The structural modifications could not, in any case, allow this gain in activity to be predicted.

The subject of the present invention is also pharmaceutical compositions containing as active principle at least one compound of formula (I), alone or in combination with one or more nontoxic, inert excipients or vehicles.

Among the pharmaceutical compositions according to the invention, there may be mentioned more especially those which are suitable for oral, parenteral or nasal administration, simple or sugar-coated tablets, sublingual tablets, hard gelatin capsules, troches, suppositories, creams, ointments, skin gels, injections, and the like.

The appropriate dosage varies according to the patient's age and weight, the nature and severity of the complaint and also the administration route. The latter may be oral, nasal, rectal or parenteral. Generally speaking, single doses range between 0.2 and 100 mg for a treatment administered in 1 to 3 doses per 24 hours.

The examples which follow illustrate the invention and in no way limit it.

The starting materials used are known products or are prepared according to known procedures.

In the examples below, the amino acids for which the abbreviations begin with a capital letter are of the L configuration. The amino acids for which the abbreviations begin with a lowercase letter are of the D configuration.

The structures of the compounds of the invention were confirmed by the standard spectroscopic techniques (nuclear magnetic resonance, infrared, mass spectrometry, etc.).

The abbreviations used in the examples are the following:

Hyp represents the (R)-4-hydroxy-L-prolyl residue of formula:

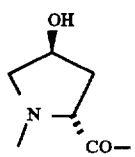

Trp-OBzl(3,5-ditrifluoromethyl) represents the residue of formula:

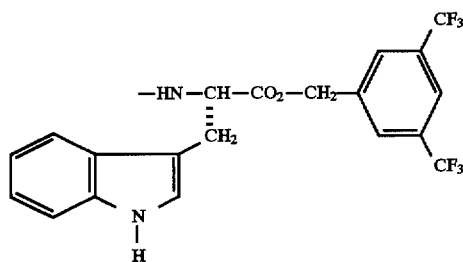

tBu represents a tert-butyl group,
Bzl represents a benzyl group,
H-Hyp(tBu)-OBzl represents the residue of formula:

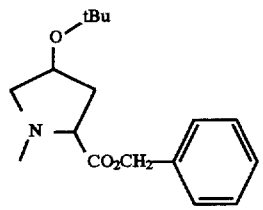

Nal-Obzl(3,5-ditrifluoromethyl) represents the residue of formula:

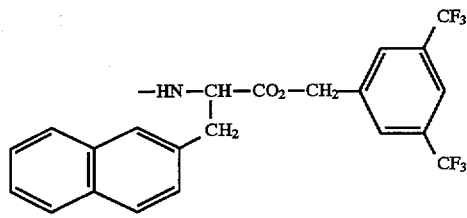

Tna-OBzl represents the residue of formula:

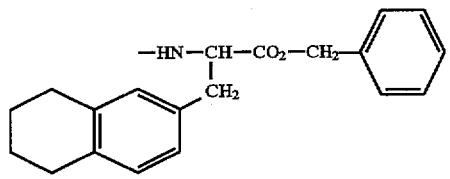

Thn-OEt represents the residue of formula:

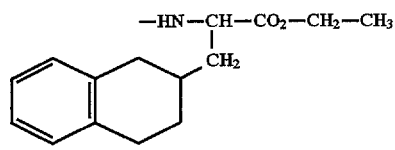

Thi-OBzl(4-Cl) represents the residue of formula:

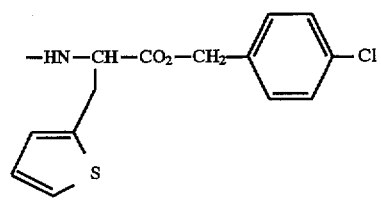

Phe-OBzl(3,5-ditrifluoromethyl) represents the residue of formula:

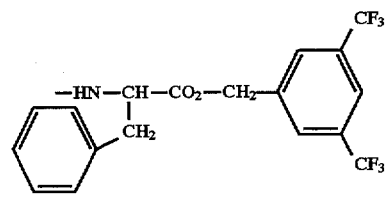

Bza-OBzl represents the residue of formula:

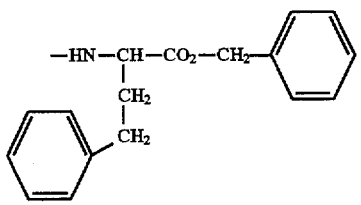

Cha-OBzl represents the residue of formula:

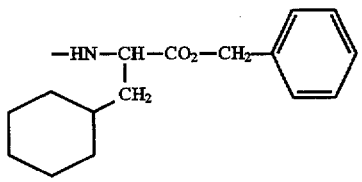

Trp-OBzl(4-MeO) represents the residue of formula:

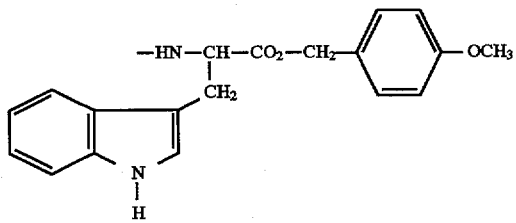

EXAMPLE 1

{1-[4-(1H-Tetrazol-5-yl)butyl]-3-indolyl}carbonyl-Hyp-Trp-OBzl(3,5-ditrifluoromethyl) potassium salt Stage A: 1-(4-Cyanobutyl)-3-indolecarboxylic acid benzyl ester 1.1 equivalents of 5-bromovaleronitrile are added to 40 mmol of 3-indolecarboxylic acid benzyl ester dissolved in tetrahydrofuran. After cooling to 0° C., 1.8 g of sodium hydride are added portionwise. After one hour of reaction at 0° C. and 14 hours at room temperature, ethyl acetate and water are added. The organic phase is separated and washed several times in succession with an aqueous phase containing hydrochloric acid followed by a basic aqueous phase. After drying and evaporation, the residue is purified by chromatography on silica gel using an ethyl acetate/pentane (2:3) mixture as solvent, and the expected product is obtained.

Stage B: 1-(4-Cyanobutyl)-3-indolecarboxylic acid 10 mmol of the compound obtained in the preceding stage, dissolved in 120 ml of methanol, are hydrogenated at atmospheric pressure for 3 and a half hours in the presence of 0.4 g of Pd/C as catalyst. After filtration through Celite and evaporation, the expected product is obtained, and is recrystallized in a chloroform/pentane mixture.

Stage C: [1-(4-Cyanobutyl)-3-indolyl]carbonyl-Hyp(tBu)-OBzl

10mmol of the product obtained in the preceding stage, 15mmol of bromotris(pyrrolidino)phosphonium hexafluorophosphate and 20 mmol of diisopropylethylamine are added to a solution containing 10 mmol of H-Hyp(tBu)-OBzl (obtained according to the process described in Patent EP 0,684,257) in 20 ml of dichloromethane. After 30 minutes at 0° C., the mixture is brought to room temperature and kept stirring for 17 hours. After evaporation, the residual oil is taken up in ethyl acetate. The organic phase is washed with aqueous sodium carbonate, citric acid and sodium chloride solutions. The expected product is then isolated by chromatography on silica gel using a dichloromethane/acetone (9:1) mixture as eluent.

Stage D: [1-(4-Cyanobutyl)-3-indolyl]carbonyl-Hyp(tBu)-OH 8 mmol of the compound obtained in the preceding stage in 20 ml of tetrahydrofuran are treated with 4 equivalents of powdered sodium hydroxide and 20 mg of tetrabutylammonium hydrogen sulfate catalyst for 16 hours at room temperature with stirring. The solution is then acidified with 350 ml of 5% citric acid. After extraction with ethyl acetate and washing, the expected product is obtained by precipitating the residue in pentane.

Stage E: [1-(4-Cyanobutyl-3-indolyl]carbonyl-Hyp(tBu)-Trp-OBzl(3,5-ditrifluoromethyl)

7 mmol of the compound obtained in the preceding stage are dissolved in 30 ml of dichloromethane and coupled with 7 mmol of H-Trp-OBzl(3,5-ditrifluoromethyl) hydrochloride in the presence of 7 mmol of 1-hydroxybenzotriazole and 7.7 mmol of 2-(1H-benzotriazol-1-yl)-1,1,3,3-tetramethyluronium tetrafluoroborate. To the mixture cooled in an ice bath, 15 mmol of diisopropylethylamine are added. The resulting mixture is held for 30 minutes at 0° C. and 14 hours at room temperature. After evaporation of the solvent, the residue is taken up with ethyl acetate. The organic phase is washed and evaporated and the expected product is obtained by precipitation in ether.

Stage F: {1-[4-(1H-Tetrazol-5-yl)butyl]-3-indolyl}-carbonyl-Hyp(tBu)-Trp-OBzl(3,5-ditrifluoromethyl)

4 mmol of the compound obtained in the preceding stage, suspended in 80 ml of toluene, are treated in succession with 12 mmol of trimethylazidosilane (TMSiN₃) and 0.8 mmol of dilbutyltin. The suspension is stirred for 20 hours at 80° C. After evaporation of the solvent, the residue is taken up with ethyl acetate. After washing of the organic phase, drying and then evaporation, the residue is purified by chromatography on silica gel using a dichloromethane/methanol (95:5) mixture, and yields the expected product.

Stage G: {1-[4-(1H-Tetrazol-5-yl)butyl]-3-indolyl}carbonyl-Hyp-Trp-OBzl(3,5-ditrifluoromethyl)

3 mmol of the product obtained in the preceding stage, dissolved in 100 ml of a trifluoroacetic acid/dichloromethane (50/50) mixture, are stirred for 90 minutes at room temperature. After precipitation in ether, the expected product is purified by preparative $C_{18}$ reversed-phase liquid chromatography using a gradient from 40 to 60% of acetonitrile/water-0.1% trifluoroacetic acid as eluent.

Stage H {1-[4-(1H-Tetrazol-5-yl)butyl]-3-indolyl}carbonyl-Hyp-Trp-OBzl(3,5-ditrifluoromethyl) potassium salt The potassium salt of the product obtained in the preceding stage is obtained by adding 2.2 mmol of potassium hydroxide in 0.1N solution in a water/acetonitrile (1:1) mixture to a cooled solution containing 2 mmol of the compound of the preceding stage. The salt is then lyophilized.

Mass Spectrum: FAB: $[M+H]^+$—m/z=849

The examples which follow were obtained according to the process described in Example 1, using the corresponding starting materials:

EXAMPLE 2

{1-[4-(1H-Tetrazol-5-yl)butyl]-3-indolyl}carbonyl-Hyp-Nal-OBzl(3,5-ditrifluoromethyl) potassium salt

EXAMPLE 3

{1-[4-(1H-Tetrazol-5-yl)butyl]-3-indolyl}carbonyl-Hyp-Tna-OBzl

EXAMPLE 4

{1-[4-(1H-Tetrazol-5-yl)butyl]-3-indolyl}carbonyl-Hyp-Thn-OEt

EXAMPLE 5

{1-[(1H-Tetrazol-5-yl)methyl]-3-indolyl}carbonyl-Hyp-Trp-OBzl(3,5-ditrifluoromethyl)

EXAMPLE 6

{1-[2-(1H-Tetrazol-5-yl)ethyl]-3-indolyl}carbonyl-Hyp-Trp-OBzl

EXAMPLE 7

{1-[3-(1H-Tetrazol-5-yl)propyl]-3-indolyl}carbonyl-Hyp-Trp-OBzl

EXAMPLE 8

{1-[5-(1H-Tetrazol-5-yl)pentyl]-3-indolyl}carbonyl-Hyp-Trp-OBzl(3,5-ditrifluoromethyl)

EXAMPLE 9

{1-[4-(1H-Tetrazol-5-yl)butyl]-3-indolyl}carbonyl-Hyp-Bza-OBzl

EXAMPLE 10

{1-[4-(1H-Tetrazol-5-yl)butyl]-3-indolyl}carbonyl-Hyp-Thi-Obzl(4-Cl)

EXAMPLE 11

{1-[4-(1H- Tetrazol-5-yl)butyl]-3- indolyl}carbonyl-Hyp-Phe-OBzl(3,5-ditrifluoromethyl)

EXAMPLE 12

{1-[4-(1H-Tetrazol-5-yl)butyl]-3-indolyl}carbonyl-Hyp-Cha-OBzl

EXAMPLE 13

{1-[4-(1H-Tetrazol-5-yl)butyl]-3-indolyl}carbonyl-Hyp-Trp-OBzl(4-MeO)

Pharmacological Study of the Compounds of the Invention

EXAMPLE 14

Affinity for the Human $NK_1$ and $NK_2$ Receptors

The affinity for the human $NK_1$ and $NK_2$ receptors was studied on IM-9 human lymphoblasts specifically expressing the $NK_1$ receptor as described by D. G. Payan et al. (J. Biol. Chem. 1986, 261, 14321–14329) and on CHO-K1 cells transfected with the $NK_2$ receptor according to the CellPhect transfection kit (Pharmacia).

The compounds of the invention showed an excellent specific affinity for the $NK_1$ receptors. The compound of Example 1 in particular possesses a KI for the $NK_1$ receptor equal to 2.4 nM, whereas that for the $NK_2$ receptor is equal to 4200 nM.

EXAMPLE 15

Tests on Isolated Smooth Muscle

In order to evaluate the functional activity of the compounds of the invention as neurokinin antagonists, two isolated preparations of smooth muscle were used: the rabbit vena cava (RVC) and the rabbit pulmonary artery without endothelium (RPA), the contractile responses of which are mediated, respectively, by the $NK_1$ and $NK_2$ receptors as shown by D. Jukic et al. (Life Sci. 1991, 49, 1463–1469).

The antagonist power of the compounds of the invention was expressed in the form of $pA_2$ as defined by O. Arunlakshana and H. O. Schild (Brit. J. Pharmacol. 1959, 14, 48–58).

The compounds of the invention showed a potent antagonist activity in relation to the $NK_1$ receptors, with a weak activity for the $NK_2$ receptors. The compound of Example 1, for example, possesses a $pA_2$ in relation to the $NK_1$ receptors equal to 8.9, whereas its $pA_2$ in relation to the $NK_2$ receptors is equal to 5.2.

EXAMPLE 16

Study of the Inhibition of Capsaicin-induced Plasma Extravasation in Guinea Pigs The effect of the compounds on the plasma extravasation caused by intravenous injection of capsaicin (200 μg/kg) in guinea pigs was evaluated in the bronchi according to the method described by Robineau et al (Eur. J. Pharmacol., 1995, 294, 677–684). The accumulation in the bronchi of Evans blue injected IV 1 minute before capsaicin was quantified by spectrophotometry after extraction of the dye with acetone. The inhibitory activity of the compounds via the intravenous route 5 minutes before capsaicin was expressed as a 50% inhibitory dose in comparison to a control group (8 animals per group). The compound of Example 1 possesses an $ED_{50}$ of 26 μg/kg iv, whereas the compound of Example 1 of Patent EP 684,257 possesses an $ED_{50}$ of 140 μg/kg, equivalent to approximately 6-fold smaller.

EXAMPLE 17

Study of the Inhibition of Substance P-induced Bronchoconstriction in Guinea Pigs The study is carried out on male Hartley guinea pigs (Charles River) weighing 300 to 400 g on average. The study is carried out on anesthetized (ethyl carbamate 1.5 g/kg) and Flaxedilcurarized (0.2 mg/kg iv) animals ventilated at a rate of 60 per minute and a volumetric flow of 10ml/kg. The animals are pretreated with pyrilamine (1 mg/kg iv) and propranolol (1 mg/kg iv).

The criterion of judgment of bronchoconstriction is the increase in tracheal insufflation pressure (TIP) induced by the iv injection of substance P at a dose of 2 nM/kg iv, each animal being its own control. Injection of the test product is performed with reference to the time TO of the injection of the product.

The results are expressed as a dose inhibiting substance P-induced bronchoconstriction by 50%, this percentage being calculated according to the following formula: (ΔTIP before product-ΔTIP after product)/ΔTIP before product (expressed as a percentage).

The compound of Example 1 possesses an $ED_{50}$ equal to 0.06 mg/kg. It is two and a half times as potent as the compound of Example 1 of Patent EP 684,257.

EXAMPLE 18

Study of Mast Cell Degranulation in Vitro

The studies are performed on rat peritoneal mast cells: male Sprague-Dawley rats weighing 350 to 400 g on average are sacrificed by inhalation of $CO_2$. A peritoneal lavage is performed with 20 ml of buffer (150 mM NaCl, 2.7 mM KCl, 0.9 mM $CaCl_2$, 3 mM $Na_2HPO_4$, 3.5 mM $KH_2PO_4$, 5.6 mM glucose, 1 mg/ml bovine serum albumin, pH 6.8).

The lavage fluid is centrifuged at 400 g for 10 min at 4° C. and the pellet is taken up in a buffer at a density of $2 \times 10^4$ mast cells/ml. The compounds are incubated at increasing concentrations for 20 min. The reaction is stopped by placing the tubes on ice and a centrifugation at 700 g for 10 min at 4° C. is performed. The supernatant and the pellet are tested by fluorimetry after condensation with O-phthalaldehyde. The histamine released from the cells into the supernatant thus assayed is expressed as a percentage of the total histamine content of the cells. In this test, the compounds of the invention do not give rise to mast cell degranulation up to a concentration of $10^{-4}$M.

Pharmaceutical Composition

EXAMPLE 19

Tablet: Preparation Formula for 1000 Tablets Each Containing 2 mg.

| | |
|---|---|
| Compound of Example 1 | 2 g |
| Hydroxypropylcellulose | 2 g |
| Wheat starch | 10 g |
| Lactose | 100 g |
| Magnesium stearate | 3 g |
| Talc | 3 g |

We claim:

1. A compound selected from the group consisting of those of formula (I):

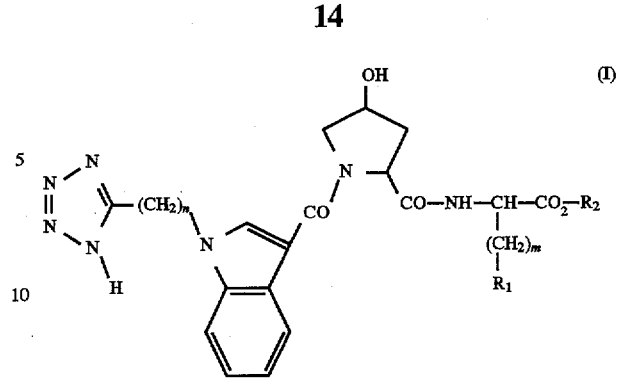

in which:

$R_1$ represents indolyl, naphthyl, tetrahydronaphthyl, thienyl, or phenyl, in each case unsubstituted or substituted with one or more halogen atoms, linear or branched ($C_1$–$C_6$)alkyl, linear or branched ($C_1$–$C_6$) alkoxy, hydroxyl, or trihalomethyl, or $R_1$ represents a ($C_3$–$C_7$)cycloalkyl group, n represents 1 to 8 inclusive, m represents 1 to 4 inclusive, $R_2$ represents benzyl which is unsubstituted or substituted with one or more halogen atoms, linear or branched ($C_1$–$C_6$)alkyl, linear or branched ($C_1$–$C_6$)alkoxy, hydroxyl, or trihalomethyl, or phenyl which is unsubstituted or substituted with one or more halogen atoms, linear or branched ($C_1$–$C_6$)alkyl, linear or branched ($C_1$–$C_6$) alkoxy, hydroxyl, or trihalomethyl, or $R_2$ represents a linear or branched ($C_1$–$C_6$)alkyl group, its enantiomers, diastereoisomers and epimers, and its addition salts with a pharmaceutically-acceptable acid or base.

2. A compound of claim 1, wherein $R_1$ represents an indolyl group.

3. A compound of claim 1, wherein $R_2$ represents an unsubstituted or substituted benzyl group.

4. A compound of claim 1, wherein $R_2$ represents a 3,5-di(trifluoromethyl)benzyl group.

5. A compound of claim 1, wherein n is equal to 4.

6. A compound of claim 1, wherein m is equal to 1.

7. The compound of claim 1 which is selected from {1-[4-(1H-tetrazol-5-yl)butyl]-3-indolyl}carbonyl-Hyp-Trp-OBzl(3,5-ditrifluoromethyl), its isomers, and its addition salts with a pharmaceutically-acceptable acid or base.

8. A method for treating living body afflicted with a condition selected from muscle contraction associated with $NK_1$ receptors, plasma extravasation and bronchoconstriction comprising the step of administering to the living body an amount of a compound of claim 1 which is effective for alleviation of said condition.

9. A pharmaceutical composition useful as a substance P antagonist comprising as active principle an effective amount of a compound of claim 1, together with one or more pharmaceutically-acceptable excipients or vehicles.

* * * * *

UNITED STATES PATENT AND TRADEMARK OFFICE
CERTIFICATE OF CORRECTION

PATENT NO. : 5,708,016
DATED : Jan. 13, 1998
INVENTOR(S) : J.L. Fauchere, N. Kucharczyk-Gentric, E. Canet, M. Lonchampt It is certified that error appears in the above-indentified patent and that said Letters Patent is hereby corrected as shown below:

Column 1, line 26:  "antagordst" should read
    -- antagonist --.

Column 2, line 27:  "formula LID" should read
    -- formula II --.

Column 14, line 43: Insert -- a -- between "treating" and "living".

Signed and Sealed this

Twenty-first Day of April, 1998

Attest:

BRUCE LEHMAN

Attesting Officer

Commissioner of Patents and Trademarks